US00PP19580P3

(12) United States Plant Patent
Davidson

(10) Patent No.: US PP19,580 P3
(45) Date of Patent: Dec. 16, 2008

(54) ***MONARDA* PLANT NAMED 'ACRADE'**

(50) Latin Name: *Monarda didyma*
Varietal Denomination: ACrade

(75) Inventor: Campbell G. Davidson, Ottawa (CA)

(73) Assignee: Her Majesty The Queen in Right of Canada as represented by the Ministry of Agriculture and Agri-Food (CA)

( * ) Notice: Subject to any disclaimer, the term of this patent is extended or adjusted under 35 U.S.C. 154(b) by 0 days.

(21) Appl. No.: 11/786,626

(22) Filed: Apr. 11, 2007

(65) Prior Publication Data

US 2008/0256674 P1 Oct. 16, 2008

(51) Int. Cl.
*A01H 5/00* (2006.01)

(52) U.S. Cl. ..... Plt./455

(58) Field of Classification Search ..... Plt./455
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of bee balm, *Monarda didyma* 'ACrade', characterized by its purple-violet blossoms that are present abundantly in June through August. The new variety is mid sized in height with a mounded plant habit, is hardy in U.S.D.A. Zones 3 to 8, and exhibits dark green slightly glossy foliage that has shown resistant to powdery mildew.

2 Drawing Sheets

Botanical classification: Monarda didyma.
Variety denomination: 'ACrade'.

BACKGROUND OF THE INVENTION

The present invention relates to a new and distinct cultivar of *Monarda didyma*. The new cultivar will be referred to hereafter by its cultivar name, 'ACrade'. 'ACrade' is a new variety of bee balm suitable for landscape plantings.

The new cultivar of *Monarda* was a selection from an on going breeding program involving open pollinated and controlled crosses at a research station in Morden, Manitoba, Canada. 'ACrade' arose from project in which the inventor planted a cultivated field in an area isolated from other cultivars of *Monarda* with hundreds of unnamed proprietary seedlings of *Monarda didyma,* allowed open-pollination to occur, collected the seeds in mass, germinated the seeds, and then lined out the seedlings in 1999. The inventor selected 'ACrade' as a single unique plant amongst the resulting seedling from this project in 2001, identified as accession no. 2000-01.

The new cultivar was first asexually propagated by softwood cuttings and rhizome division in Morden, Manitoba, Canada in 2001. Asexual propagation in Morden, Manitoba, Canada and St. Paul, Minn. by these techniques have determined that the characteristics of this cultivar are stable and are reproduced true to type in successive generations.

SUMMARY OF THE INVENTION

The following traits have been repeatedly observed and represent the characteristics of the new *Monarda* as observed for a period of four years in Morden, Manitoba, Canada and St. Paul, Minn. These attributes in combination distinguish 'ACrade' as a unique cultivar of *Monarda.*

1. 'ACrade' exhibits purple-violet colored blossoms.
2. 'ACrade' blooms abundantly in June through August.

3. 'ACrade' exhibits dark green, slightly glossy foliage.
4. 'ACrade' is mid-sized in height (somewhat dwarf) and exhibits a mounded plant habit.
5. 'ACrade' has shown good resistance to powdery mildew (Sphaerotheca pannosa var. rosa) under the conditions tested.
6. 'ACrade' is hardy in U.S.D.A. Zones 3 to 8.

The new cultivar of *Monarda* can be readily distinguished from other cultivars. 'ACrade' is distinguishable from all cultivars of *Monarda* known to the Inventor. *Monarda* 'Petite Delight' (U.S. Plant Pat. No. 10,784) and *Monarda didyma* 'AChall' (U.S. Plant Pat. pending application Ser. No. 11/64851)—examiner has permission to replace this reference with a patent no. if available) are the closest comparison cultivars known to the inventor. They are both similar to 'ACrade' in their relative short stature and resistance to powdery mildew, however 'Petite Delight' differs in having larger flowers, glossier foliage, and is taller in plant height. 'AChall' differs in having flowers that are redder in color (red-purple) and an upright oval plant habit.

BRIEF DESCRIPTION OF THE DRAWING

The accompanying colored photographs illustrate the overall appearance and distinct characteristics of the new *Monarda*, 'ACrade', as grown outdoors in a trial plots in St. Paul, Minn. The plants were approximately two years in age and the photographs were taken in mid summer of 2005.

Figure 1:
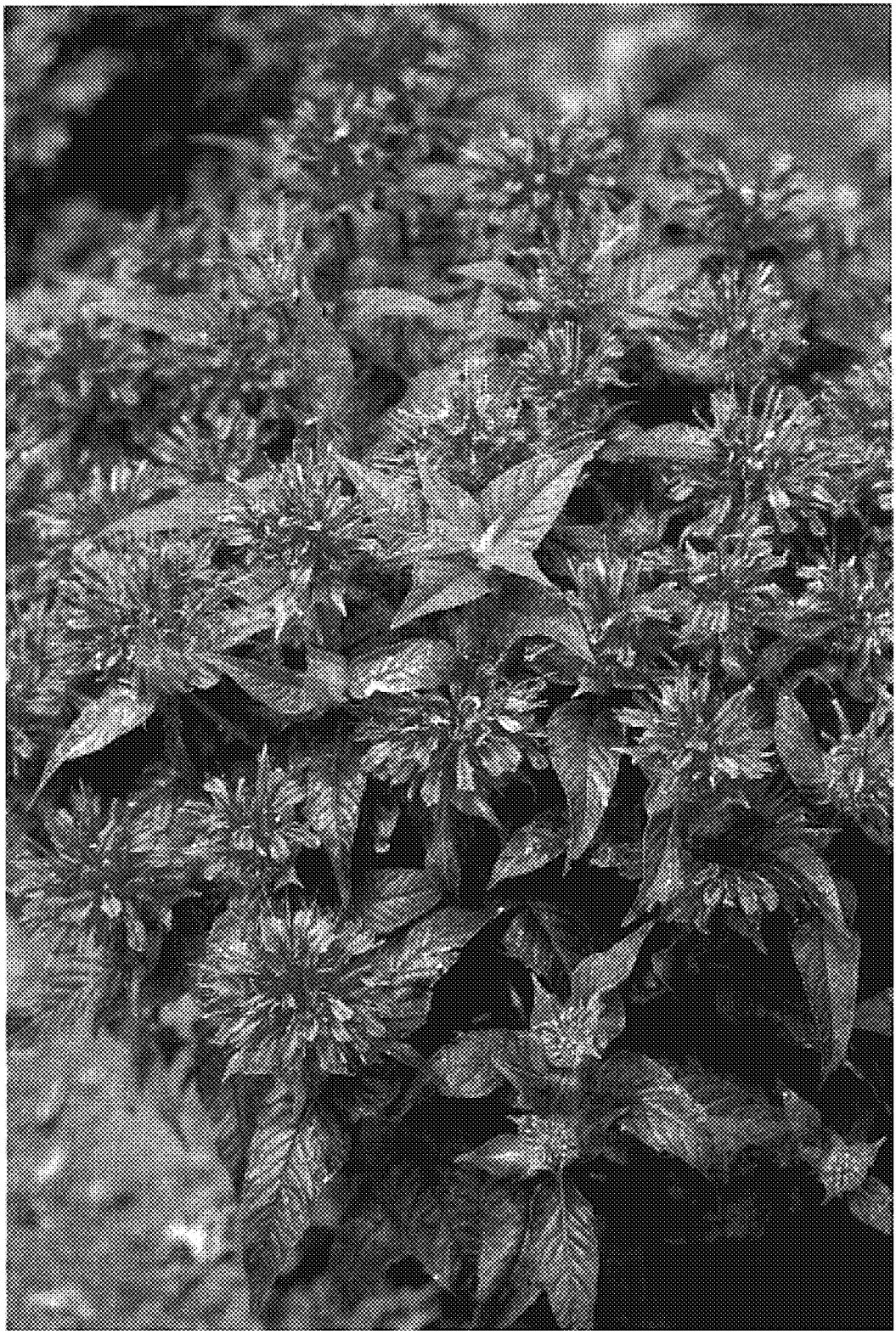
FIG. 1 provides a view of a plant of 'ACrade' in bloom.
Figure 2:
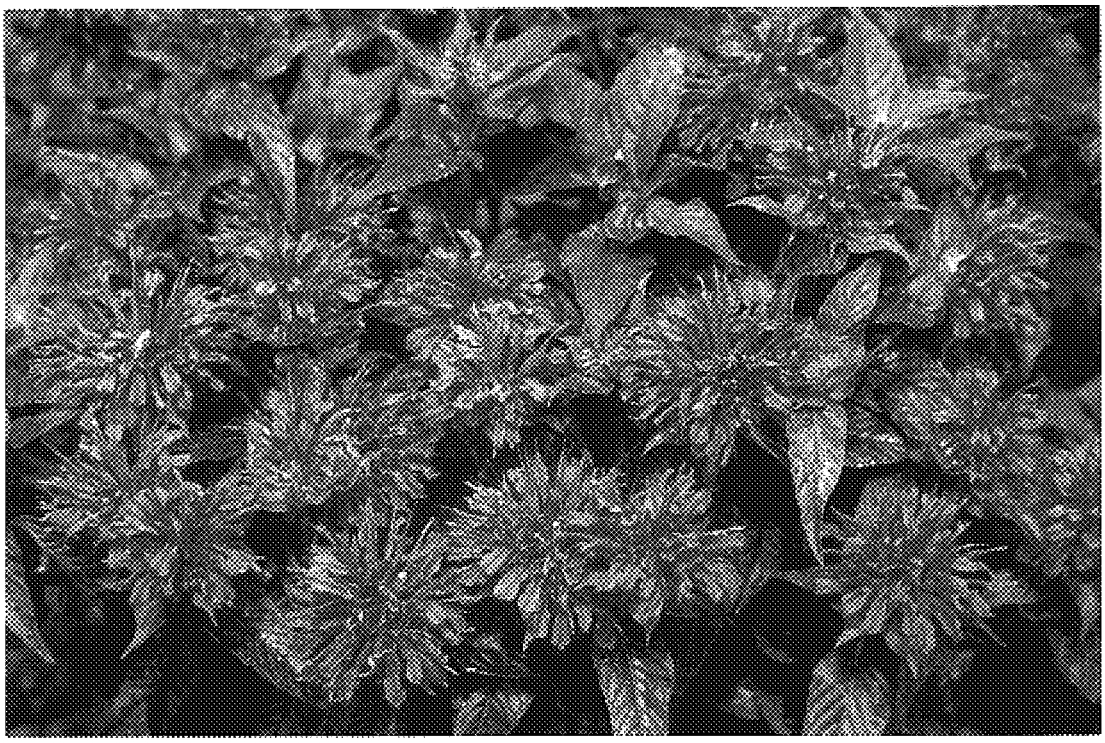
FIG. 2 provides a close-up view of flowers of 'ACrade'.

The colors in the photographs are as close as possible with digital photography techniques available, the color values cited in the detailed botanical description accurately describe the colors of the *Monarda.*

DETAILED BOTANICAL DESCRIPTION

The following is a detailed description of the new cultivar as observed for four years as grown outdoors under field conditions in Morden, Manitoba, Canada and St. Paul, Minn. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Monarda didyma* 'ACrade'.

*Parentage.*—Proprietary, unnamed selections of *Monarda didyma* produced by open pollination.

*Blooming habit.*—Abundantly in June through August, can be prolonged and denser with deadheading and pruning.

*Plant habit.*—Mounded.

*Height and spread.*—Mid-sized in height (somewhat dwarf), reaches about 32 to 40 cm in height and 40 to 50 cm in spread.

*Cold hardiness.*—U.S.D.A. Zone 3 to 8.

*Diseases and pests.*—Good degree of resistance observed to powdery mildew (Sphaerotheca pannosa var. rosa), no insect problems observed.

*Propagation.*—Softwood stem cuttings or by rhizome division.

*Growth.*—Vigorous and strong.

Stem description:

*Stem shape.*—Square.

*Stem color.*—Young; 137C, mature wood; 147A with highlights of 200C, particularly around nodes.

*Stem surface.*—Pubescent when young, becomes woody as it matures.

*Lateral branches.*—Average of 6 per 35 cm stem stem, average of 8.1 cm in length in the middle of branch and 6.2 cm in length on the top 12 cm of the stem, average of 3 cm in diameter, average internode length of 2.75 cm.

Foliage description:

*Leaves.*—Opposite arrangement, ovate to ovate-lanceolate in shape, rounded base, acuminate apex, serrulate margins, slightly glossy texture on upper surface and lower surface, average of 6.5 cm in length and 3.2 cm in width, color: young foliage upper surface; 137A, young foliage lower surface; color between 137C and 138B, mature foliage upper surface; 137A, mature foliage lower surface; a color between 137B and 137C.

*Petioles.*—Average of 1 cm in length and 3 mm in diameter, color of upper surface and lower surface 144A, pubescent surface.

Inflorescence description:

*Inflorescence type.*—Borne terminally in whorls or as verticillaster.

*Inflorescence number.*—1 per lateral stem.

*Inflorescence fragrance.*—Pungent mint.

*Inflorescence size.*—Average of 3.85 cm in depth and 4.5 cm in diameter.

*Peduncles.*—Average of 2.5 cm in length and 3.4 mm in diameter, surface is glabrous with pubescence on edges, color is 137B with highlights of 138B on edges.

*Bracts.*—About 7 per verticillaster, average of 4.2 cm in length and 2.1 cm in width, ovate to lanceolate in shape, surface is slightly glossy, color of upper surface is 137B with 137B to 137C towards margin and apex, color of lower surface is between 137C and 137D with 137B to 137C towards margin and apex.

*Floret buds.*—Elongated tube in shape, average of 2.4 cm in length and 2.1 mm in width prior to opening, color is 77A fading to 77B towards base, surface is glabrous.

*Floret longevity.*—About 5 to 7 days, depending on temperature.

*Floret type.*—Tubular.

*Floret quantity.*—Average of 41 per verticillaster.

*Floret size.*—Average of 3.5 mm in diameter and 4.5 cm in depth.

*Sepals.*—Typically 21 per verticillaster, lanceolate in shape, margin is entire, upper surface and lower surface are glabrous, average of 1.65 cm in length and 3.25 cm in width, apex is acuminate, base is rounded, color of upper surface on opening florets; 144A suffused with 145A near base, color of lower surface on opening florets; 144B suffused with 144A on apex and margin, fully open florets upper surface; color between 144A to 144B suffused with 145B at base and on main vein, fully open florets lower surface; 144B suffused with 144A on apex and margin.

*Petals.*—2, the upper (lip) is hooded, erect with a mucronate-like apex extended at a 45° to lip and entire margins while the lower is 3 lobed and more spreading, glabrous surface, average of 4.5 mm in length and 3.5 mm in width, color: opening florets upper surface; 80A with 74A on center depression of lip and base 76D, opening florets lower surface; between 81A and 81B fading to 82C towards base, fully open florets upper surface; 80B with main tube 81A, fully open florets lower surface; 81B with main tube 80A.

*Pistils.*—1, stigma is an average of 2.1 mm in length and 0.8 mm in width with color 84C, style is an average of 2.4 cm in length with color 75A suffused with 77A and 155A on portion exerted outside of floret, ovary is very small containing one ovule.

*Stamens.*—Typically 2 per floret, filaments are about 1.85 cm in length and 76D in color, anthers are an average of 2.9 mm in length, an average of 1.4 mm in width and 78D in color, pollen is scarce and 13C in color.

*Seeds.*—1 per floret, average of 0.7 mm in length and 0.4 mm in diameter, oval to rice shaped, color is 199C.

I claim:

1. A new and distinct cultivar of *Monarda* plant named 'ACrade' as herein illustrated and described.

* * * * *